(12) United States Patent
Cramer

(10) Patent No.: US 8,648,219 B2
(45) Date of Patent: Feb. 11, 2014

(54) METHOD FOR PURIFYING GLYCERIN AND PRODUCTS OBTAINED THEREFROM

(76) Inventor: James Cramer, Chelsea, MI (US)

( * ) Notice: Subject to any disclaimer, the term of this patent is extended or adjusted under 35 U.S.C. 154(b) by 275 days.

(21) Appl. No.: 12/860,451

(22) Filed: Aug. 20, 2010

(65) Prior Publication Data

US 2012/0046496 A1  Feb. 23, 2012

(51) Int. Cl.
*C07C 31/22* (2006.01)
*C07C 29/86* (2006.01)

(52) U.S. Cl.
USPC .......................................... 568/869; 568/870

(58) Field of Classification Search
None
See application file for complete search history.

(56) References Cited

U.S. PATENT DOCUMENTS

| | | | |
|---|---|---|---|
| 6,537,436 | B2 | 3/2003 | Schmidt et al. |
| 7,126,032 | B1 | 10/2006 | Aiken |
| 2009/0178928 | A1* | 7/2009 | Groos et al. ............... 204/541 |

FOREIGN PATENT DOCUMENTS

| | | |
|---|---|---|
| CN | 101182281 | 5/2008 |
| CN | 101265160 | 9/2008 |
| CN | 101423456 | 5/2009 |
| KR | 10-2009-0094480 | 9/2009 |

OTHER PUBLICATIONS

Translation of KR 10-2009-0094480 (dated Sep. 8, 2009). Obtained from <http://kposd.kipo.go.kr:8088/up/kpion/> . Accessed on Jul. 3, 2009.*
"Table 2. Fatty acid composition of rapeseed and low erucic (canola) oil compared to olive oil, soybean and sunflower." Published by FAO.org. Accessed on Mar. 25, 2013. Obtained from <ftp://ftp.fao.org/es/esn/food/bio-10t.pdf>.*

* cited by examiner

*Primary Examiner* — Alicia L Otton
(74) *Attorney, Agent, or Firm* — Brinks Gilson & Lione

(57) ABSTRACT

A method and system for purifying crude glycerin is provided in which a mixture is formed by blending glycerin, water, an organic solvent, and an acid. The acid being capable of reacting with soap impurities to form lipids that are soluble in the organic solvent and ionic salts that are soluble in the glycerin and water. Liquid-liquid extraction separates and partitions the organic solvents and lipids away from the glycerin, water, and ionic salts with the organic solvent and lipids being reclaimed for future use. Any residual trace amount of organic solvent that remains in the glycerin and water is separated and removed through the use of a clarifier system, with the formation of micro-bubbles arising from a diffuser facilitating the separation. Prior to collection of the purified glycerin product, the ionic salts are removed from the mixture through the use of an ionic exchange resin, electrodialysis, or electrodeionization, followed by the water being removed by evaporation. The resulting purified glycerin exhibits a purity level on the order of about 99.7% or more.

10 Claims, 3 Drawing Sheets

METHOD FOR PURIFYING GLYCERIN AND PRODUCTS OBTAINED THEREFROM

FIELD

This disclosure relates generally to a method and system for purifying a by-product or waste stream formed in a manufacturing process. More specifically, this invention relates to the purification of glycerin formed during the production of biodiesel fuel from fats or oils.

BACKGROUND

Glycerin may be obtained as a by-product from the transesterification of triglycerides (i.e., biodiesel fuel production) in an amount as high as about 11 percent of the overall products formed. Recent advances made in biodiesel fuel production have encouraged the development of many new industrial applications that use glycerin. For example, glycerin can be used as a raw material in the industrial production of propylene glycol, epichlorohydrin, acrylic acid, or polyhydroxybutyrate. Glycerin in a pure form also has many uses, such as for example, in pharmaceuticals and cosmetics.

The basic chemical reaction for the catalyzed production of biodiesel fuel is shown in Equation 1 below. In this reaction, a fat or oil (such as soybean oil, rape seed oil, etc.) is reacted with a short chain alcohol in the presence of a catalyst to produce glycerin and compounds capable of being used as biodiesel fuel. The short chain alcohol (ROH), which preferably is methanol or ethanol, is usually used in excess to facilitate a high conversion of oil or fats to biodiesel fuel. The catalysts commonly used are basic in nature and easily dispersible in the alcohol reactant. Examples of such catalysts, include sodium hydroxide, potassium hydroxide, sodium methylate, or the like. As shown in Equation 1, the R', R", and R'" moieties indicate fatty acid chains, such as palmitic, stearic, oleic, and linoleic acids, that are found in naturally occurring oils and fats.

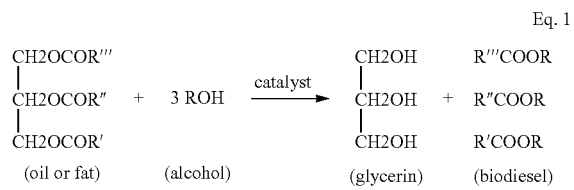

Eq. 1

The glycerin formed as a byproduct during the transesterification of triglycerides is normally of a crude or impure grade. The typical impurities found in the glycerin by-product include the catalyst, various soaps, methanol, lipids, and water. Since the catalyst is typically neutralized at the end of the transesterification reaction, the catalyst normally exists in solution as a salt.

Purification is required to transform the crude glycerin to a state suitable for use in existing or emerging applications. The salt content in crude glycerin, which often ranges from 5 percent to 7 percent, makes conventional purification techniques cost intensive. Examples of conventional purification methods include vacuum distillation and bleaching with activated carbon. However, such purifying processes are expensive and the elimination of process steps that require the regeneration or disposal of a consumable material, such as activated carbon, is desirable. Accordingly, there exists a need to provide an improved method and system for purifying glycerin and products obtained therefrom that are more cost effective than conventional methods and systems.

SUMMARY

The present disclosure provides a method and a system for use in purifying crude glycerin obtained as a by-product or waste stream in a manufacturing environment, such as encountered in biodiesel fuel production. According to one embodiment of the present disclosure, the method adjusts the acidity of a mixture formed by blending the crude glycerin with water, an acid, and an organic solvent. The addition of the acid causes soaps present in the crude glycerin as impurities to be converted into lipids that are soluble in the organic solvent and ionic salts that are soluble in the glycerin or water. A form of liquid-liquid extraction is then utilized to separate or partition the organic solvent and lipids away from the glycerin, water and ionic salts. The organic solvent may be recovered and reused by being blended with the crude glycerin at the start of the process. The lipids may be recovered and used in a secondary process, such as a reactant in the formation of an amide surfactant.

After the bulk of the organic solvent is removed via liquid-liquid extraction, a trace amount of organic solvent can still reside in the glycerin, water, and ionic salt mixture. This trace amount of organic solvent is removed through the use of a clarifier in which the formation of micro-bubbles created by a diffuser facilitates the separation of the trace organic solvent from the glycerin, water, and salt mixture. Separation and removal of the trace organic solvent is accomplished through a means similar to that used in the liquid-liquid extraction. Final purification steps include exposing the glycerin, water, and salt mixture to at least one of an ion exchange resin, electrodialysis, or electrodeionization to remove the ionic salts followed by drying the glycerin and water to remove the water component. The dried glycerin is collected as a purified glycerin product exhibiting a purity level on the order of 99.7% or more.

Another embodiment of the present disclosure provides a system for use in the purification of crude glycerin in accordance with the method disclosed herein. More specifically, the purification system incorporates a blending subsystem for mixing the glycerin with water, an acid, and an organic solvent; extraction subsystem for partitioning and removing the organic solvent and lipid impurities, a clarifier subsystem for removing any remaining trace amounts of organic solvent, a solvent reclaim subsystem for recovering the organic solvent and lipids, an electrodialysis or electrodeionization subsystem for removing ionic salts, a drying subsystem for evaporating the water, and a collection vessel for collecting the refined or purified glycerin product. Optionally, the purification system may also incorporate a pretreatment subsystem for filtering the crude glycerin or an ultra-filtration subsystem for filtering the glycerin after processing through the clarifier subsystem. Preferably, the system is operated as a continuous purification system with a flow rate on the order of about 15 gallons per minute or more.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

Figure 1:
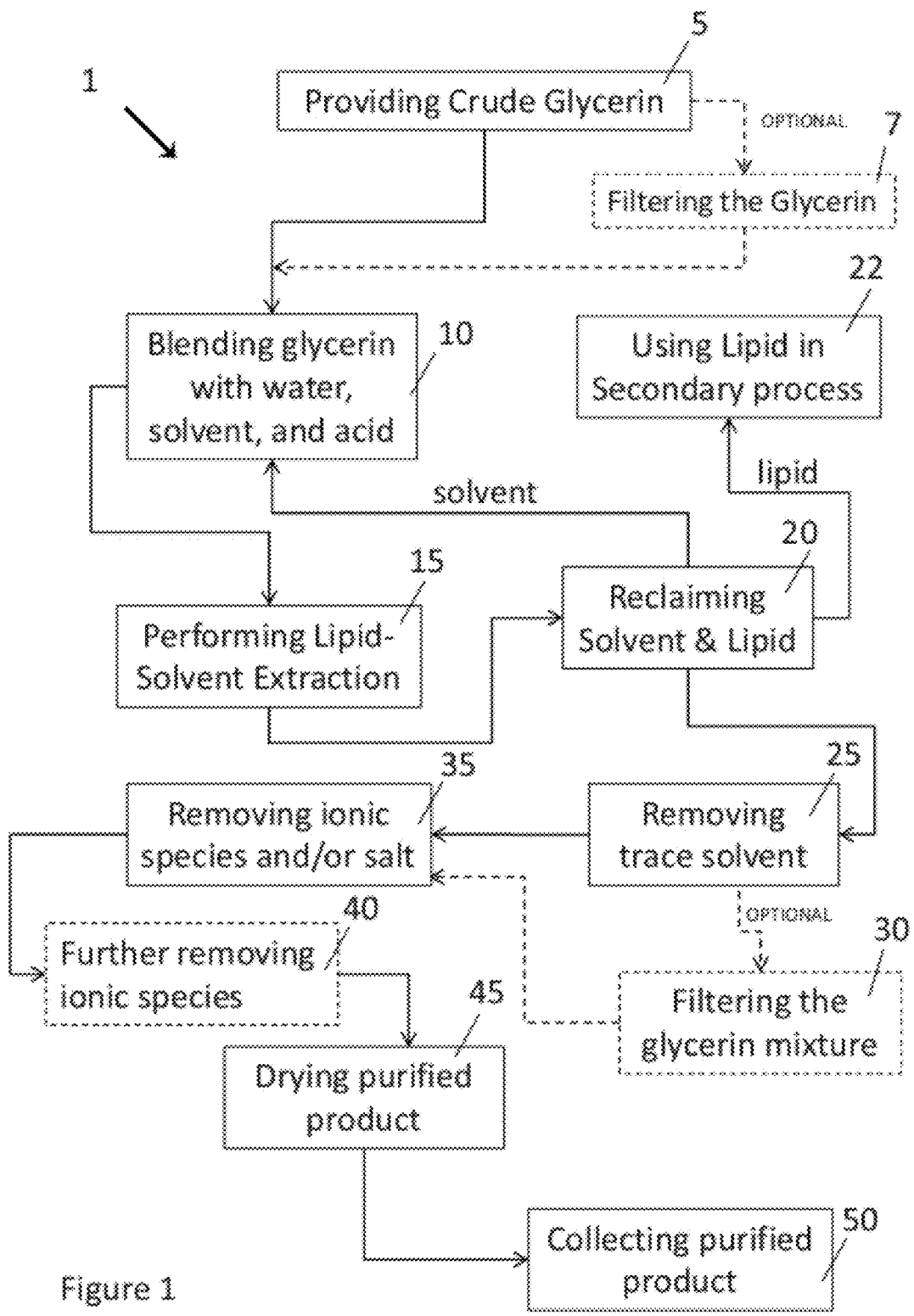
FIG. 1 is a schematic representation of a method of purifying glycerin according to the teachings of the present disclosure.

The following description is merely exemplary in nature and is in no way intended to limit the present disclosure or its application or uses. It should be understood that throughout the description and drawings, corresponding reference numerals indicate like or corresponding parts and features.

The present disclosure generally provides a method of purifying crude glycerin obtained as a by-product or waste stream during a manufacturing or production process. Referring to FIG. 1, the method 1 basically comprises providing and introducing a source 5 of crude glycerin into a vessel for blending 10 with water, an acid, and an organic solvent. Preferably, the crude glycerin is obtained as a by-product during the transesterification of fats and oils to form biodiesel fuel. The purity of the crude glycerin may be on the order of about 80-90% with impurities or contaminants, including but not limited to water, catalyst salts, soaps, fatty acids, and other lipids or lipid derivatives, making up the remainder.

When desirable or necessary, the crude glycerin may be filtered 7 to remove any solid particulate, agglomerates, or other matter organic non-glycerin (MONG) that may have formed and accumulated during the separation or collection of the glycerin by-product from the biodiesel fuel manufacturing process. One skilled-in-the-art will understand that such filtration 7 may be done as part of the biodiesel fuel manufacturing process, immediately prior to being blended 10 in the purification process 1 described herein, or somewhere in between.

The crude glycerin is blended 10 with a predetermined amount of water, an acid, and an organic solvent to form a mixture. The ratio of the amount of water added to the amount of glycerin present is preferably on the order of about 1:1. The amount of acid added is based upon the amount necessary to adjust the pH of the mixture to be less than about 4.0 with a pH in the range of 3.5 to 4.0 being desirable or preferred. The type of acid blended with the glycerin may include, but not be limited to, hydrochloric acid or sulfuric acid. The acidic nature of the mixture is believed to facilitate the conversion of the various soaps and other lipid derivatives present in the glycerin to fatty acids/lipids that are soluble in the organic solvent. During the production of biodiesel fuel, soaps or salts are formed by the reaction of fatty substances with the basic catalysts. The conversion of the soaps to fatty acids may also lead to the formation of various salts and ionic species that are compatible with the glycerin and water in the mixture.

The organic solvent is preferably a food grade solvent with food grade mineral spirits being preferred. One skilled-in-the-art will understand that other organic solvents may be utilized provided that the solvent is compatible with fatty acids and lipids and substantially immiscible with the water and/or glycerin.

Still referring to FIG. 1, the blended mixture is allowed to separate and partition into a top component layer and a bottom component layer. This step in the method may be described as lipid-solvent extraction 15. This extraction step 15 primarily allows the organic solvent and water/glycerin combination to form into separate layers based on their density differential. The organic solvent being less dense than the water/glycerin combination typically becomes the top component layer, while the water/glycerin combination becomes the bottom component layer. Thus the top component layer includes the organic solvent along with any dissolved fatty acids and lipids. Preferably, the fatty acids and lipids present in the top component layer includes those that have a carbon chain or backbone of sixteen or more carbon atoms with a chain in the range of about sixteen to eighteen carbon atoms being desirable. The bottom component layer comprises the glycerin, water, ionic salts or species and a trace amount of residual organic solvent.

The top layer component is removed or extracted away from the bottom component layer. The organic solvent is subsequently separated from the lipids and reclaimed 20. The reclaimed organic solvent may subsequently be re-used in the blending step 10 to mix with glycerin, water, and an acid to form the mixture. The reclaimed fatty acids and lipids may be used as a raw material in another or secondary process. One example of such a secondary process is a production process that uses fatty acids or lipids as a reactant for the formation of an amide surfactant.

Still referring to FIG. 1, the trace amount of organic solvent is removed 25 from the bottom component layer by placing the bottom component layer into a clarifier subsystem. The introduction of air or another gas into the bottom component layer may facilitate the separation of the trace organic solvent from the glycerin, water, and ionic salts. The micro-bubbles formed upon the aeration of the bottom component layer is believed to assist or facilitate the movement of the trace organic solvent through the bulk layer of glycerin and water to form a separate or portioned solvent layer that can be extracted or removed in a manner similar to that described in the extraction step 15 for the top component layer. The organic solvent recovered in this manner may also be used as part of the organic solvent that is mixed with the glycerin, water, and acid in the blending step 10.

Optionally, the glycerin may be subjected to an ultra-filtration process 30 after processing to remove trace amounts of solvent 25. The use of ultra-filtration 30 may be important when the method 1 is operated as a continuous process having a high rate of effluent flow between steps.

The remaining combination of glycerin, water, and ionic salts obtained after the removal of trace solvent 25 is then subjected to removal of the ionic salts 35 by exposing the combination to at least one of an electrodialysis (ED) procedure, an electrodeionization (EDI) procedure, or an ion exchange resin. Optionally, a combination of the above procedures may be utilized 40 to ensure that the ionic species are effectively removed. One skilled-in-the-art will understand that both ED and EDI represent procedures that utilize electricity to remove ionic impurities from a polar medium, such as water.

After removal of the ionic species, the remaining glycerin and water combination is subjected to a drying process 45 in which the water is removed. Upon completion of the drying process 45, the glycerin may be collected 50 as a purified product. Preferably, the purified product will exhibit a purity of about 99.7% or higher.

The method 1 may be performed in either a continuous or batch manner. Preferably, the method represents a continuous process having effluent flowing between process steps at a predetermined rate. The rate of continuous flow may be on the order of about 15 gallons per minute or more depending upon the scale or size of the system. The method 1 provides multiple benefits over conventional methods used to purify crude glycerin in a production environment. Such benefits include but are not limited to the method 1 functioning as a continuous process with little to no use of any consumable media and resulting in a minimal amount of waste being generated, which ultimately correlates with low disposal costs. In other words, the method 1 of the present disclosure represents a more cost effective process for purifying glycerin.

Figure 2:
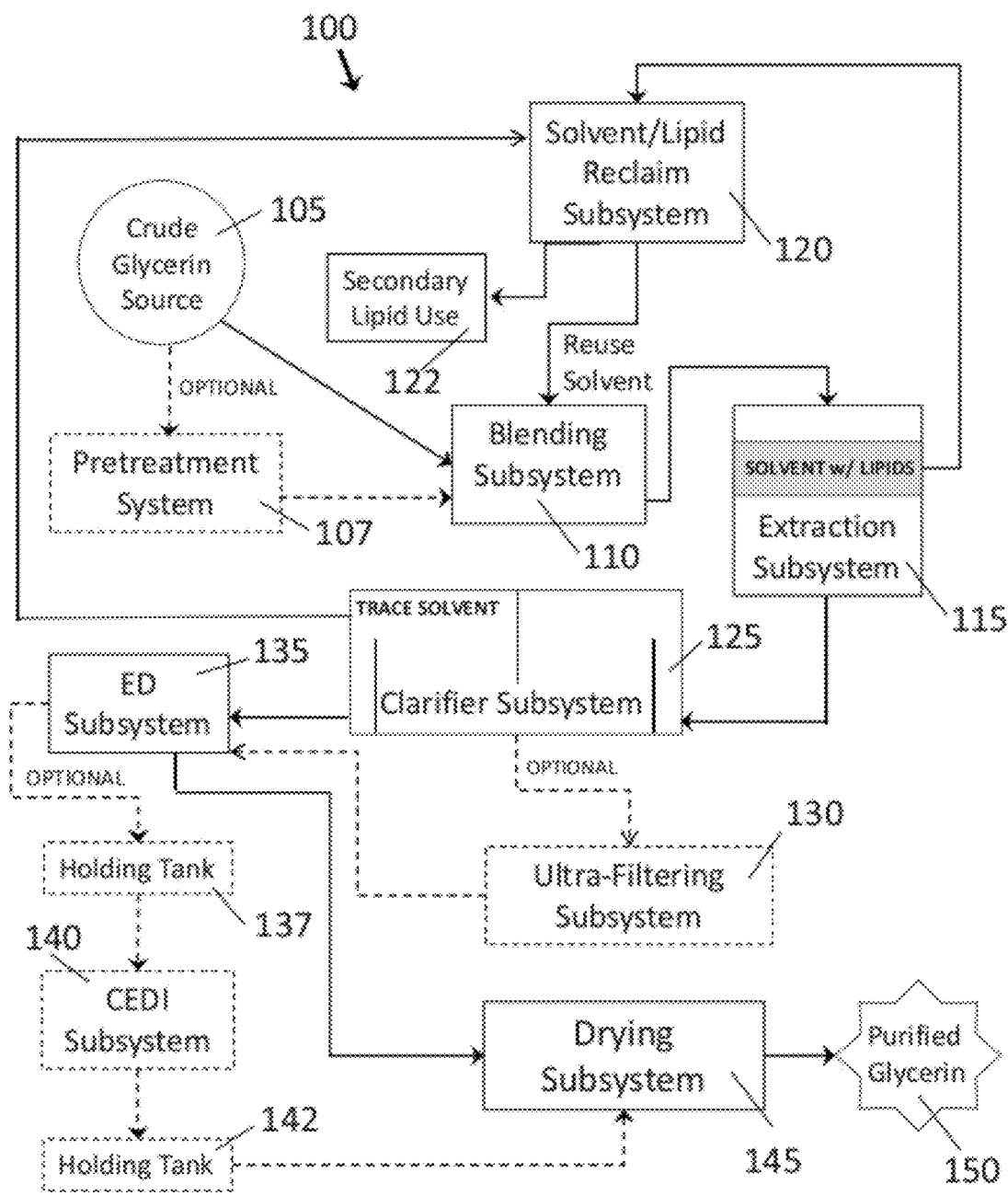
FIG. 2 is a schematic representation of a system used to purify glycerin according to the method of FIG. 1.

Another objective of the present disclosure to provide a system capable of purifying crude glycerin according to the method 1 described herein. Referring to FIG. 2, such a system 100 includes a source of crude glycerin 105. The glycerin source 105 may be a storage vessel or a flow line delivering the glycerin directly from a production process. When the production process is related to the formation of biodiesel fuel via transesterification reactions, the crude glycerin may also include a mixture of mono-, di-, and triglycerides, alcohol, water, and some fatty acid alkyl esters, as well as residual catalyst or salts (i.e., ionic species).

The crude glycerin source is connected to a blending subsystem 110 and delivers the crude material to the blending subsystem 110. One skilled-in-the-art will understand that the connection between the various components in the system 100 may be accomplished by any means known, including but not limited to flow lines, pipes, or conduits and that the system 100 may include peripheral equipment (not shown), such as flow meters, pumps, and pH meters to name a few, without exceeding the scope of the present disclosure.

The blending subsystem 110 may comprise a tank or vessel equipped with an agitator to blend the crude glycerin with a predetermined amount of water, acid, and organic solvent. Optionally, the crude glycerin may flow through a pretreatment subsystem 107 prior to being introduced into the blending subsystem 110. This pretreatment subsystem 107 may comprise various means of filtering the crude glycerin to remove any solid organic matter that is not glycerin (MONG) including any agglomerates and/or particulates.

The size of the blending subsystem 110 can be determined from the flow rate one desires to achieve through the system 100 and the amount of water, acid, and organic solvent that will be added to the glycerin to form a mixture. Once blended, the mixture is allowed to flow into an extraction subsystem 115. Such an extraction subsystem 115 is a tank that is sized to allow the residence time necessary for the organic solvent and the water/glycerin combination to separate or partition. A tank having a height in excess of about 15 feet may be utilized with the mixture of glycerin/water/acid/organic solvent entering the tank via an inlet located proximate to the bottom of the tank. The organic solvent, which contains soluble lipids or lipid derivatives, separates from the mixture to form the top component layer, while the glycerin, water, and ionic salts form the bottom component layer. The top component layer may be removed, skimmed, or extracted from the mixture leaving the bottom component layer for further processing. Such an extraction subsystem 115 may leave a residual or trace amount of organic solvent in the bottom component layer.

The extraction subsystem 115 utilizes a concept known to one skilled-in-the-art as liquid-liquid extraction or solvent extraction and partitioning. The extraction subsystem separates compounds based on their relative solubilities in two different immiscible liquids. In other words, in the extraction subsystem 115 a substance can be removed from a mixture by preferentially dissolving that substance in a suitable solvent that is immiscible with another major liquid (e.g., glycerin and water) present in the mixture.

The top component layer may subsequently be transferred to a reclamation subsystem 120 in which the organic solvent and the lipids are separated and collected. The reclaimed organic solvent may be reutilized as a portion of the solvent added to the blending subsystem 110 to form the blended mixture. The reclaimed lipids may be utilized in secondary processes, such as a chemical intermediate or reactant for the production of an amide surfactant.

Figure 3:
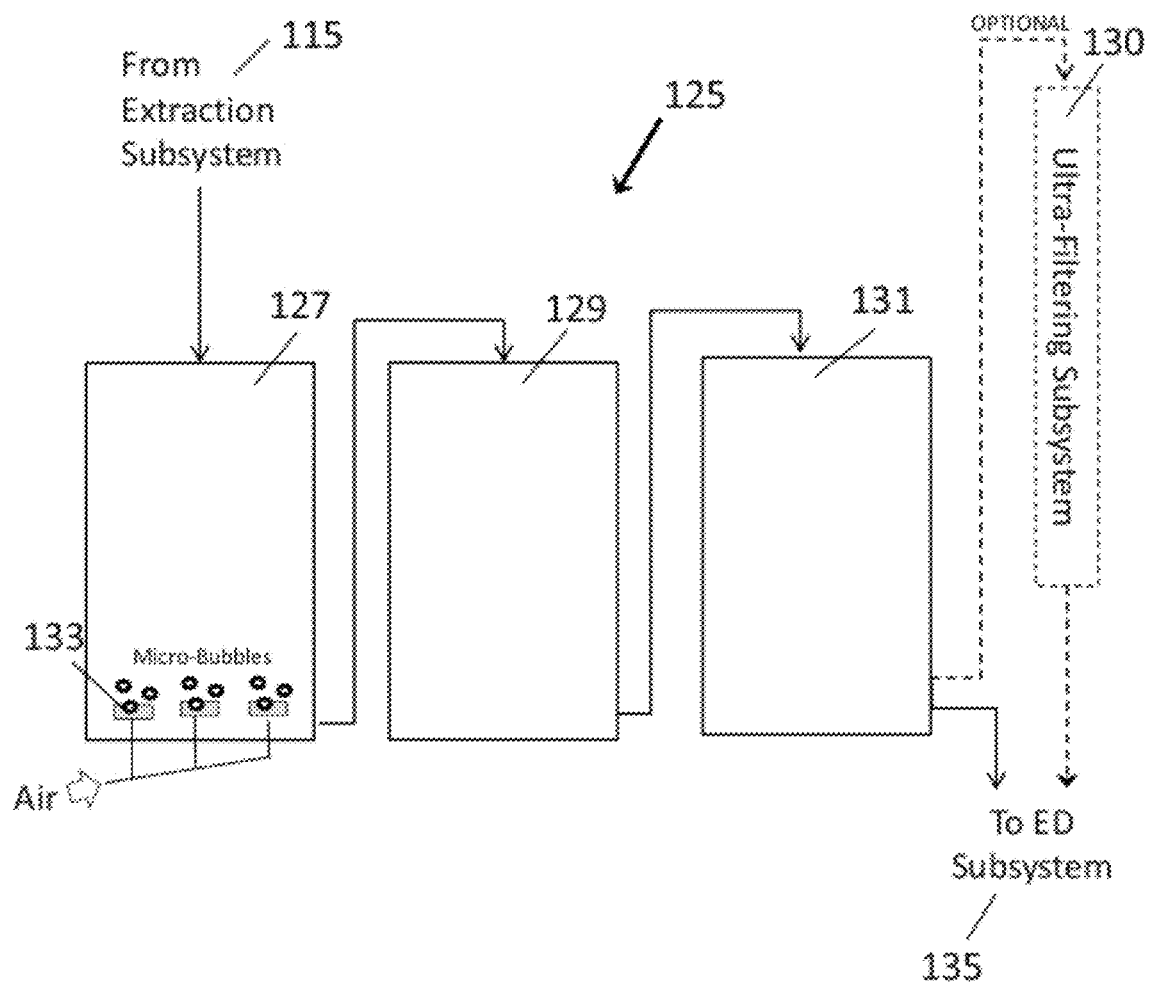
FIG. 3 is a schematic representation of the clarifier subsystem used in the system of FIG. 2 according to one aspect of the present disclosure.

The bottom component layer is transferred from the extraction subsystem 115 to a clarifier subsystem 125. The clarifier subsystem 125 is adapted to remove the trace amount organic solvent from the bottom component layer. As shown in FIG. 3, the clarifier subsystem 125 may comprise one or more chambers 127, 129, 131 similar to that utilized in the extraction subsystem 115. The chambers 127, 129, 131 may be cascaded together in which the bottom component layer flows from the bottom of the one chamber into the top of the next chamber with the effluent flowing from the final chamber being transferred to an electrodialysis (ED) subsystem 135. In each chamber, the residual organic solvent is allowed to separate from the glycerin/water combination. In one or more chambers a source of aeration in the form of one or more diffusers 133 may be located proximate the bottom of each chamber 127, 129, 131. These diffusers 133 allow for the introduction of a gas, such as air or nitrogen among others, into the bottom component layer through the formation of micro-bubbles. Although not wanting to be held to theory, the micro-bubbles are believed to assist or facilitate the separation of the organic solvent from the glycerin/water combination. The micro-bubbles, as well as the trace organic solvent can be removed or extracted when it accumulates near the surface or top of the bottom component layer. When desirable or necessary, prior to transferring the glycerin from the clarifier subsystem 125 to an ED subsystem 135 as described below, the glycerin may be placed into and through an ultra-filtration subsystem 130.

The bottom component layer is then transferred from the clarifier subsystem 125 or the optional ultra-filtration subsystem 130 to at least one of an electrodialysis (ED) subsystem 135, an electrodeionization subsystem (EDI), or through a column of an ion exchange resin (IER) in order to remove or eliminate the presence of ionic salts or species in the bottom component layer. When necessary or desired the bottom component layer exiting the ED, EDI, or IER subsystem 135 may be placed through a second 140 such subsystem for further purification. Upon exiting the ED, EDI, or IER subsystem 135, 140 the bottom component layer may be stored in a holding tank 137, 142 prior to further processing. One skilled in the art will understand that electrodialysis and electrodeionization are electrochemical separation processes in which ions are transferred through selective ion exchange membranes from one solution to another by means of a DC voltage.

The bottom component layer with the ionic species removed is then transferred into a drying subsystem 145 to remove the water from the glycerin via evaporation. The drying subsystem 145 may be any type of heating or drying system known to one skilled-in-the-art, including but not limited to conventional thermal ovens or systems that utilize infrared or microwave sources for evaporating the water. Upon removal of the water from the glycerin in the bottom component, the bottom component may be collected as a purified glycerin product 150.

A person skilled-in-the-art will recognize that any measurements described in the present disclosure, such as the measurement of pH, are standard measurements that can be obtained by a variety of different test methods.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of purifying crude glycerin recovered as a by-product or waste stream in a manufacturing process, the purification method comprising the steps of:
   providing crude glycerin contaminated with impurities;
   blending the crude glycerin with a predetermined amount of water, an acid, and an organic solvent to form a mixture; the acid reacting with the impurities to form ionic salts and lipids in the mixture;
   allowing the mixture to separate and partition into a top component layer and bottom component layer;
   extracting the top component layer from the bottom component layer in the mixture; the top component layer including a majority of the organic solvent and the lipids; the bottom component layer including the water, the glycerin, the ionic salts and a trace amount of the organic solvent;
   placing the bottom component layer of the mixture into a clarifier; the clarifier adapted to remove the trace amount of the organic solvent; wherein the clarifier used to remove the trace amount of the organic solvent from the bottom component layer incorporates a plurality of chambers in which the bottom component layer and the trace amount of organic solvent are allowed to separate and partition; at least one of the chambers includes a diffuser adapted to create a flow of micro-bubbles in order to facilitate the separation of the trace amount of organic solvent from the bottom component layer,
   placing the bottom component layer through at least one selected from the group of an ion exchange resin, an electrodialysis device, and an electrodeionization device in order to remove the ionic salts from the glycerin and the water;
   drying the glycerin and water to remove the water; and
   collecting the glycerin as a purified product.

2. The purification method of claim 1, wherein the step of providing the crude glycerin uses the glycerin contaminated with impurities including soaps in an amount of up to about 25% by weight.

3. The purification method of claim 1, wherein the step of providing crude glycerin uses glycerin obtained from a manufacturing process that produces a biodiesel fuel product through transesterification reactions.

4. The purification method of claim 1, wherein the step of blending the crude glycerin with water, an acid, and an organic solvent forms the mixture exhibiting a pH that is less than about 4.0.

5. The purification method of claim 1, wherein the method further comprises a filtering step to remove solid contaminants prior to the step of blending the crude glycerin with water, acid, and solvent to form a mixture.

6. A method of purifying crude glycerin recovered as a by-product or waste stream in a manufacturing process, the purification method comprising the steps of:
   providing crude glycerin contaminated with impurities;
   blending the crude glycerin with a predetermined amount of water, an acid, and an organic solvent to form a mixture; the acid reacting with the impurities to form ionic salts and lipids in the mixture; wherein the organic solvent used in the blending to form the mixture is food grade mineral spirits,
   allowing the mixture to separate and partition into a top component layer and bottom component layer;
   extracting the top component layer from the bottom component layer in the mixture; the top component layer including a majority of the organic solvent and the lipids; the bottom component layer including the water, the glycerin, the ionic salts and a trace amount of the organic solvent;
   placing the bottom component layer of the mixture into a clarifier; the clarifier adapted to remove the trace amount of the organic solvent;
   placing the bottom component layer through at least one selected from the group, of an ion exchange resin, an electrodialysis device, and an electrodeionization device in order to remove the ionic salts from the glycerin and the water;
   drying the glycerin and water to remove the water; and
   collecting the glycerin as a purified product.

7. The purification method of claim 6, wherein the step of providing the crude glycerin uses the glycerin contaminated with impurities including soaps in an amount of up to about 25% by weight.

8. The purification method of claim 6, wherein the step of providing crude glycerin uses glycerin obtained from a manufacturing process that produces a biodiesel fuel product through transesterification reactions.

9. The purification method of claim 6, wherein the step of blending the crude glycerin with water, an acid, and an organic solvent forms a mixture exhibiting a pH that is less than about 4.0.

10. The purification method of claim 6, wherein the method further comprises a filtering step to remove solid contaminants prior to the step of blending the crude glycerin with water, an acid, and an organic solvent to form a mixture.

* * * * *